(12) United States Patent
Hsieh et al.

(10) Patent No.: US 9,566,400 B2
(45) Date of Patent: Feb. 14, 2017

(54) NEBULIZER WITH NEGATIVE PRESSURE STRUCTURE

(71) Applicant: MICRO BASE TECHNOLOGY CORPORATION, Bade, Taoyuan County (TW)

(72) Inventors: Shu-Pin Hsieh, Bade (TW); Tun-Ying Fang, Bade (TW); Mei-Hui Huang, Bade (TW); Yu-Ju Su, Bade (TW); Chin-Jung Chang, Bade (TW); Yu-De Su, Bade (TW)

(73) Assignee: MICRO BASE TECHNOLOGY CORPORATION, Bade, Taoyuan County (TW)

( * ) Notice: Subject to any disclaimer, the term of this patent is extended or adjusted under 35 U.S.C. 154(b) by 707 days.

(21) Appl. No.: 13/677,328

(22) Filed: Nov. 15, 2012

(65) Prior Publication Data

US 2013/0125878 A1    May 23, 2013

(30) Foreign Application Priority Data

Nov. 18, 2011 (TW) .............................. 100221854 U (51) Int. Cl.
| | |
|---|---|
| *A61M 15/00* | (2006.01) |
| *B05B 17/06* | (2006.01) |
| *B05B 1/08* | (2006.01) |
| *B05B 7/30* | (2006.01) |
| *B05B 1/30* | (2006.01) |
| *A61M 11/02* | (2006.01) |
| *B05B 15/02* | (2006.01) |
| *B05B 17/00* | (2006.01) |

(52) U.S. Cl.
CPC ............... *A61M 11/02* (2013.01); *B05B 15/02* (2013.01); *B05B 17/0646* (2013.01)

(58) Field of Classification Search
None
See application file for complete search history.

(56) References Cited

U.S. PATENT DOCUMENTS

| | | | | |
|---|---|---|---|---|
| 4,465,234 A | * | 8/1984 | Maehara et al. | ............ 239/102.2 |
| 5,042,467 A | * | 8/1991 | Foley | ................ A61M 15/0086 128/200.14 |
| 5,398,850 A | * | 3/1995 | Sancoff | ............. A61M 5/14593 222/386.5 |
| 6,196,218 B1 | * | 3/2001 | Voges | ....................... 128/200.14 |
| 6,923,383 B1 | * | 8/2005 | Joshi | .................... A01M 1/2072 239/302 |

(Continued)

*Primary Examiner* — Tan-Uyen (Jackie) T Ho
*Assistant Examiner* — Eric Bryant
(74) *Attorney, Agent, or Firm* — Leong C. Lei (57) ABSTRACT

A nebulizer with a negative pressure structure includes a nebulization body, a carrying cavity, a nebulizing element and a negative pressure generating element. The carrying cavity is provided for carrying a nebulized liquid and has a through hole. The nebulizing element is installed at the through hole and includes a piezoelectric driving unit and a nebulizing plate disposed on a side of the piezoelectric driving unit. The negative pressure generating element is formed on the carrying cavity and provided for changing the volume of the carrying cavity or removing air from the carrying cavity to reduce the air pressure in the carrying cavity, so as to nebulize a liquid of low surface tension or high viscosity effectively.

1 Claim, 11 Drawing Sheets

(56) References Cited

U.S. PATENT DOCUMENTS

| | | | |
|---|---|---|---|
| 7,896,006 B2* | 3/2011 | Hamano | A61M 11/041 128/204.15 |
| 2002/0158156 A1* | 10/2002 | Joshi et al. | 239/590 |
| 2005/0067503 A1* | 3/2005 | Katase | 239/373 |
| 2006/0243274 A1* | 11/2006 | Lieberman | A61M 11/005 128/200.14 |
| 2008/0163869 A1* | 7/2008 | Nobutani | A61M 15/025 128/200.23 |
| 2009/0281483 A1* | 11/2009 | Baker | A61M 1/0058 604/28 |
| 2010/0071687 A1* | 3/2010 | Hsieh et al. | 128/200.14 |
| 2011/0226236 A1* | 9/2011 | Buchberger | 128/200.23 |
| 2011/0233302 A1* | 9/2011 | Lin et al. | 239/102.2 |
| 2012/0318260 A1* | 12/2012 | Hsieh et al. | 128/200.23 |

* cited by examiner

NEBULIZER WITH NEGATIVE PRESSURE STRUCTURE

CROSS-REFERENCE TO RELATED APPLICATIONS

This non-provisional application claims priority under 35 U.S.C. §119(a) on Patent Application No(s). 100221854 filed in Taiwan, R.O.C. on Nov. 18, 2011, the entire contents of which are hereby incorporated by reference.

BACKGROUND OF THE INVENTION

1. Field of the Invention

The present invention generally relates to nebulizers, and more particularly to the nebulizer with a negative pressure structure.

2. Description of the Related Art

In general, a conventional nebulizer is comprised of a circular piezoelectric plate, a nebulizing plate, a fixing plate and a cavity. For the nebulization of a liquid having a general surface tension, if the total air and liquid pressure value in the cavity is greater than or equal to the external air pressure value (approximately equal to one 1 atmospheric pressure), the pressure at the inner side and the outer side of the nebulizing plate reaches an equilibrium, and a nebulized liquid stored in the cavity can be attached onto an inner side of the nebulizing plate, so that the nebulized liquid will not spill out from the spray hole, so as to achieve the effects of preventing the spray hole from being clogged easily and nebulizing the liquid effectively.

However, for a liquid having a low surface tension, the surface tension cannot be maintained stably due to the too-low surface tension, so that the liquid will not spill from the inner side to the outer side of the spray hole of the nebulizing plate. If the nebulizing liquid has a spilling speed greater than the nebulization speed, the liquid will spill continuously from the spray hole of the nebulizing plate to cover the surface of the nebulizing plate and result in clogging the spray hole and failing to nebulize the liquid effectively.

If the air pressure in the cavity has a positive pressure value, and the nebulized liquid is attached onto the spray hole of the nebulizing plate, and the external air pressure is smaller than the air pressure and liquid pressure in the cavity, then the nebulized liquid in the cavity will spill out from the spray hole of the nebulizing plate to achieve a pressure equilibrium state. As to the liquid with a low viscosity or a general viscosity, the small molecular weight and coherence force between molecules can be separated during the process of passing droplets of the liquid through the spray hole of the nebulizing plate spray hole, so as to achieve an effective nebulization.

However, as to a liquid of a high viscosity, the liquid has a greater molecular weight and Van der Waals' forces between molecules, the adherence force between molecules drives the liquid to spill out from the spray hole of the nebulizing plate, when the molecules of the liquid pass through the spray hole of the nebulizing plate for anebulization. As a result, the spray hole is covered by the liquid and fails to nebulize the liquid effectively. If a negative pressure state can be maintained in the cavity, the nebulized liquid is attached onto the spray hole of the nebulizing plate, and the external air pressure is greater than the pressure in the cavity, then the external air will move from the hole of the nebulizing plate into the cavity for a pressure equilibrium to reduce the spilling and facilitate the nebulized liquid and the external air to be exchanged by vibrations of the nebulizing plate and nebulize the liquid effectively.

SUMMARY OF THE INVENTION

To achieve the aforementioned objective, the present invention provides a nebulizer with a negative pressure structure comprising a nebulization body, a carrying cavity, a nebulizing element and a negative pressure generating element. The carrying cavity is provided for carrying a nebulized liquid and has a through hole. The nebulizing element is installed at the through hole and includes a piezoelectric driving unit and a nebulizing plate disposed on a side of the piezoelectric driving unit. The negative pressure generating element is formed on the carrying cavity and provided for changing the volume of the carrying cavity or removing air from the carrying cavity to reduce the air pressure in the carrying cavity.

DETAILED DESCRIPTION OF THE PREFERRED EMBODIMENTS

The technical contents of the present invention will become apparent with the detailed description of preferred embodiments and the illustration of related drawings as follows.

Figure 1:
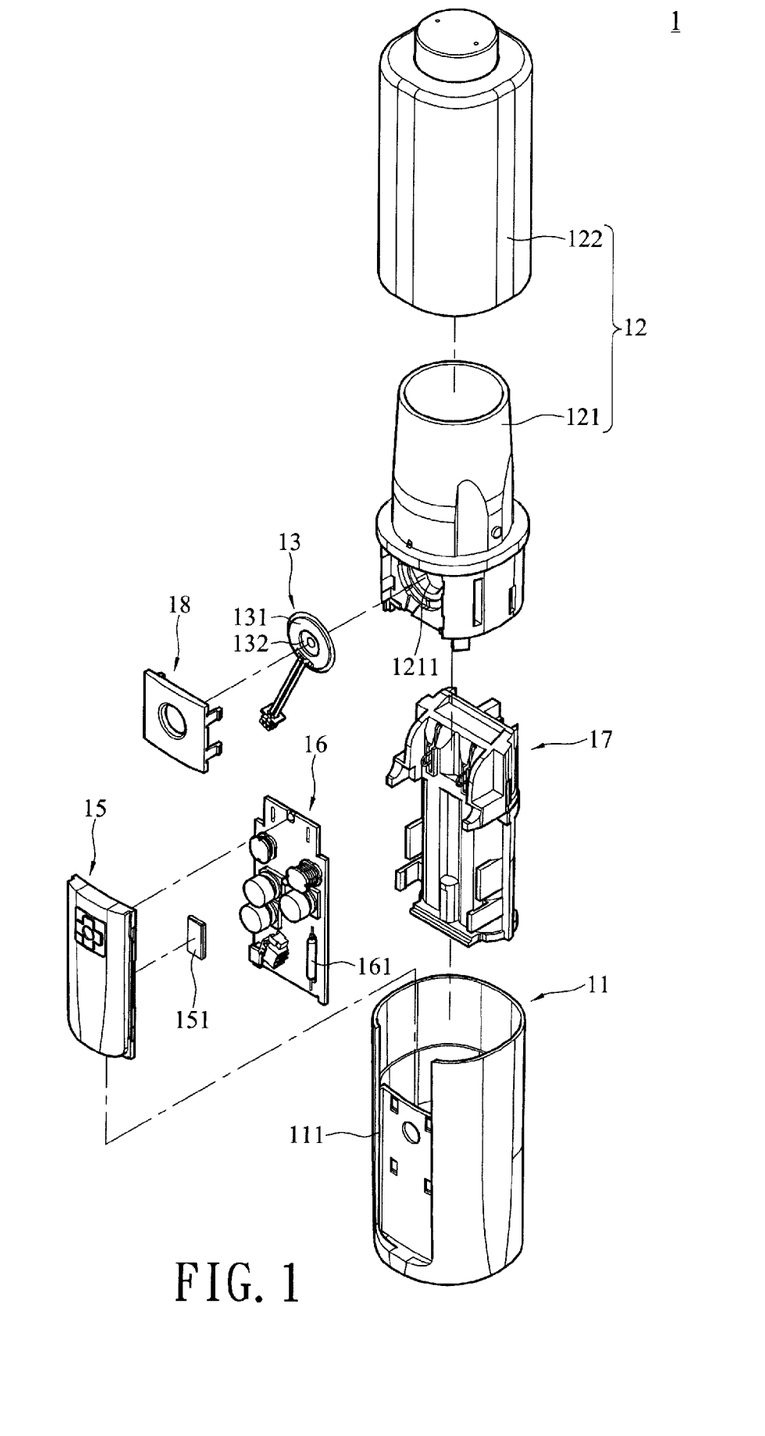
FIG. 1 is an exploded view of a nebulizer with a negative pressure structure of a first preferred embodiment of the present invention.
Figure 2:
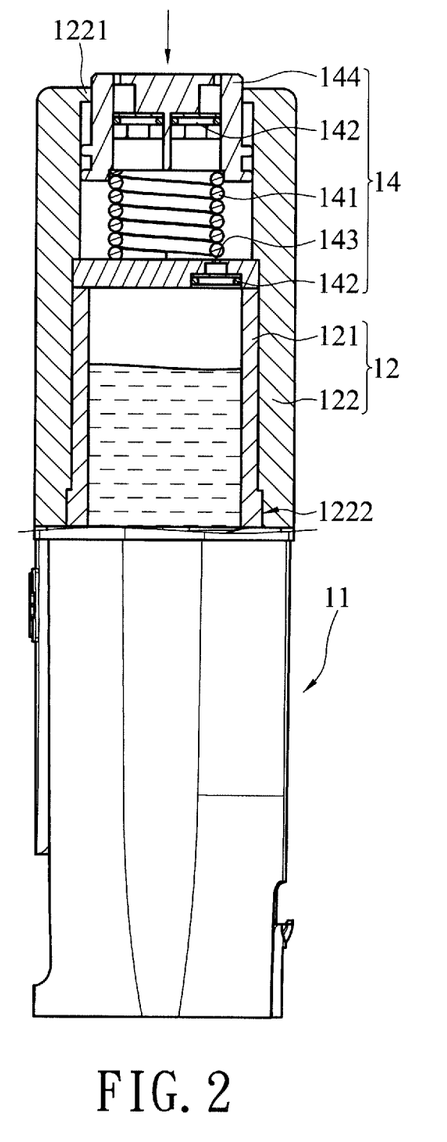
FIG. 2 is a first schematic view of a nebulizer that produces a negative pressure effect in accordance with the first preferred embodiment of the present invention.
Figure 3:
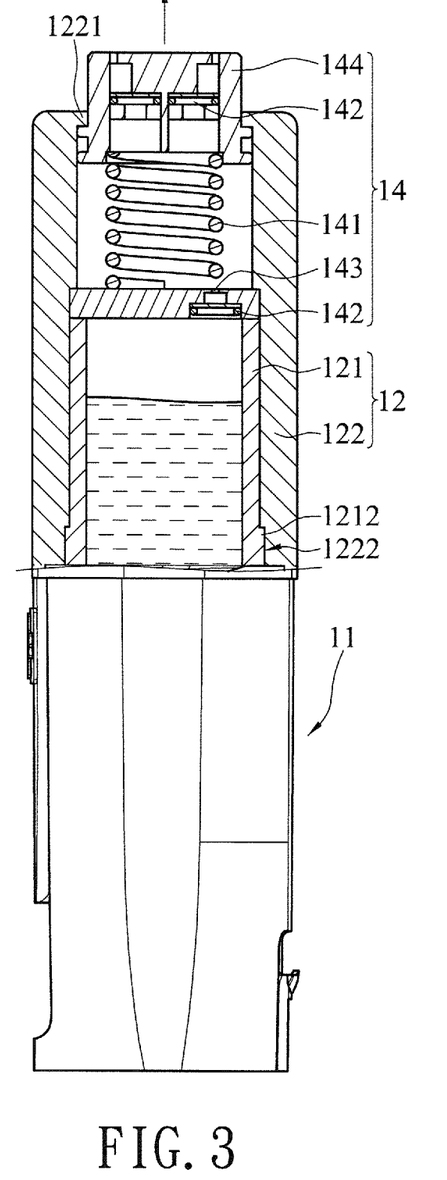
FIG. 3 is a second schematic view of a nebulizer that produces a negative pressure effect in accordance with the first preferred embodiment of the present invention.

With reference to FIGS. 1 to 3 for an exploded view of a nebulizer and first and second schematic views of the nebulizer that produces a negative pressure in accordance with the first preferred embodiment of the present invention respectively, the nebulizer 1 comprises a nebulization body 11, a carrying cavity 12, a nebulizing element 13, a negative pressure generating element 14, a slide element 15, a printed circuit board 16, a battery holder 17 and a spray hole cover 18.

The nebulization body 11 is made of plastic or metal. In this preferred embodiment, the nebulization body 11 is substantially in a cylindrical shape and provided for containing the slide element 15, the printed circuit board 16 and the battery holder 17. The printed circuit board 16 is electrically coupled to the nebulizing element 13 and has a magnetic switch 161, and the battery holder 17 is provided for installing a battery to supply electric power required by the nebulizer 1. The spray hole cover 18 is provided for covering a through hole 1211 of the carrying cavity, and the through hole 1211 is provided for installing the nebulizing element 13. In addition, the nebulization body 11 has a slide rail 111 disposed on an outer wall of the nebulization body 11 for installing the slide element 15 thereon. The slide element 15 has a magnet 151 used for changing the relative position of the magnetic switch 161 to turn on or off the nebulizer 1.

The carrying cavity 12 is disposed in the nebulization body 11 and extended upwardly, and the carrying cavity 12 is comprised of an inner cup body 121 and an outer cup body 122, and the inner cup body 121 is provided for carrying a nebulized liquid 9. The inner cup body 121 has a containing space formed therein for carrying a nebulized liquid 9.

The nebulizing element 13 is comprised of a piezoelectric driving unit 131, a nebulizing plate 132 and a structure plate (not shown in the figure). The piezoelectric driving unit 131 can be a piezoelectric driving unit of any type such as a piezoelectric ceramic device, and the structure plate can be used for driving the piezoelectric driving unit 131 to stably oscillate the nebulizing plate 132 and facilitate the nebulization process, and the nebulizing plate 132 is clamped between the piezoelectric driving unit 131 and the structure plate.

The slide element 15 is provided for sliding to an ON position or an OFF position on the nebulization body 11 to turn on or off the nebulizer 1 respectively.

The negative pressure generating element 14 is comprised of an inner cup body 121 and an outer cup body 122. The outer cup body 122 is comprised of a spring 141, a one-way exhaust valve 142, an air-hole plate 143 and a pressing portion 144. The pressing portion 144 is disposed at a position of an upper section of the outer cup body 122, and the one-way exhaust valve 142 is installed in the pressing portion 144, and the air-hole plate 143 is installed at a position of a middle section in the outer cup body 122. The spring 141 is installed in the outer cup body 122 of the carrying cavity 12, wherein an end of the spring 141 abuts the pressing portion 144, and the other end of the spring 141 abuts the air-hole plate 143. The external peripheries of the pressing portion 144, the one-way exhaust valve 142 and the one-way exhaust valve 142 have a O-ring (not shown in the figure) separately, and a sealed space is formed by a contact portion between the inner cup body 121 and the outer cup body 122, and another sealed space is formed by a contact portion between the outer cup body 122 and the pressing portion 144.

In addition, the one-way exhaust valve 142 can be added and installed on the air-hole plate 143, such that a user can press the pressing portion 144 to decrease the volume occupied by the spring 141 and push the air occupied in the volume of the spring 141 out from the one-way exhaust valve 142 of the pressing portion. The pressing portion 144 resumes its initial position by the spring 141, so that the pressure in the volume occupied by the spring 141 is reduced to drive and open the one-way exhaust valve 142 of the air-hole plate 143 and discharge the air from the inner cup body 121 to the volume occupied by the spring 141. When the pressing portion 144 is pressed continuously, the air is discharged from the inner cup body 121 to produce a negative pressure state of the air, so that the one-way exhaust valve 142 can be added and installed onto the air-hole plate 143 to prevent the pressing portion 144 from being pressed repeatedly that may cause an incomplete seal between the outer cup body 122 and the pressing portion 144 and also prevent the incomplete seal that may keep the external pressure in the inner cup body 121 in equilibrium and maintain the in the negative pressure state in the inner cup body 121.

Wherein, the outer cup body 122 has a tenon 1221 formed at the top of the outer cup body 122 and provided for latching the inner cup body 121, so that the pressing portion 144 will not fall out from the outer cup body 122 due to the upwardly exerted resilience force of the spring 141.

In addition, an embedding slot 1222 is formed on an inner side of the outer cup body 122, and a protrusion is formed on an outer side of the inner cup body 121, and the outer cup body 122 is sheathed on the inner cup body 121, and the protrusion is latched to an end of the embedding slot, so that the outer cup body 122 is fixed on the inner cup body 121. When a user presses the pressing portion 144, the spring 141 is compressed and deformed, and the pressing portion 144 is moved in a direction towards the inner cup body 121. Now, the volume of the carrying cavity 12 is increased and the air in the carrying cavity 12 is compressed to increase the pressure in the carrying cavity 12 and discharged from the one-way exhaust valve 142

When the use releases the pressing portion 144, the spring resumes its original position to drive the pressing portion 144 to move in a direction away from the outer cup body 122 and return the pressing portion 144 to its original position. Now, the volume of the carrying cavity 12 is equal to the volume before the inner cup body 121 is pressed, but some air has been discharged from the one-way exhaust valve 142 and decreased. In addition, air is allow to enter but not to exit, due to the characteristic of the one-way exhaust valve 142, so that the value of the pressure in the carrying cavity 12 is smaller than the atmospheric pressure and in a negative pressure state.

Since the carrying cavity 12 is situated in a negative pressure state, therefore when the nebulized liquid in the carrying cavity 12 is a nebulized liquid (with a viscosity of approximately 1.5~20 cp which is greater than that of water) with a low surface tension (such as 55 dyne/cm), the air-liquid exchange produces droplets by vibrations based on the principle of nebulization, and the nebulized liquid and external air can achieve the exchange more effectively by the nebulizing plate in the negative pressure state, so as to provide a more effective nebulization.

With reference to FIGS. 4 and 5 for the second preferred embodiment of the present invention, the difference between this preferred embodiment and the previous preferred embodiment resides on the structure of the carrying cavity 22 and the negative pressure generating element 24 only, and the structure and functions of other elements are the same as those of the first preferred embodiment and thus will not be repeated. In FIGS. 4 and 5, the negative pressure generating element 24 is an elastic plug covered onto a side of the carrying cavity 22 and the elastic plug has a one-way exhaust valve 241 and a latch portion 242, and a tenon 221 is formed at an end of the carrying cavity 22 and corresponding to the latch portion 242, and the one-way exhaust valve 241 is formed at an end of the elastic plug.

Figure 4:
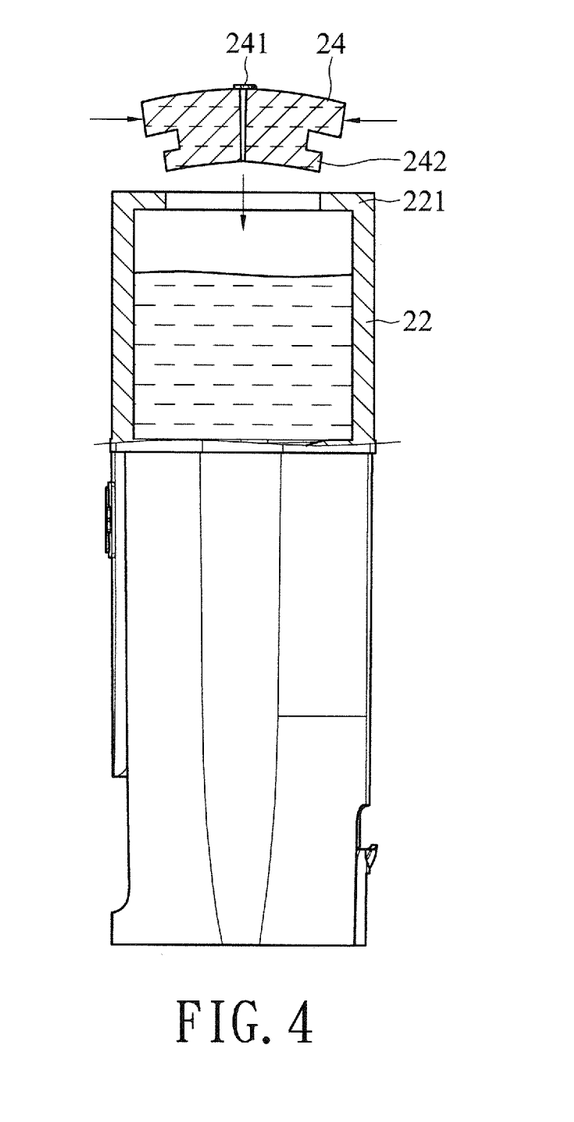
FIG. 4 is a first schematic view of a nebulizer that produces a negative pressure effect in accordance with a second preferred embodiment of the present invention.
Figure 5:
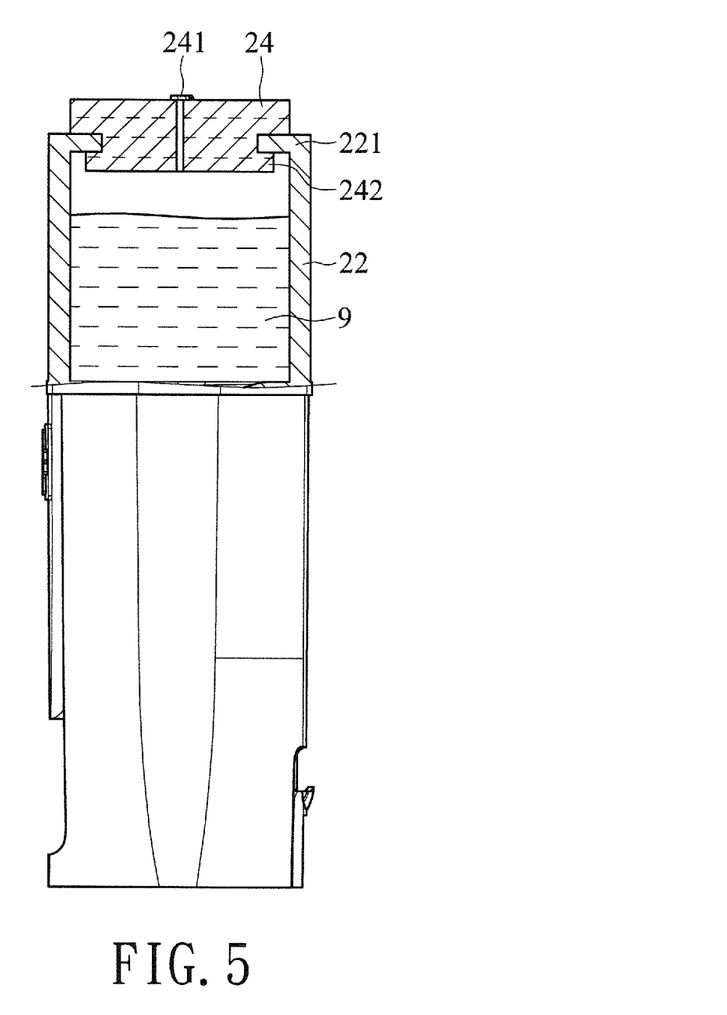
FIG. 5 is a second schematic view of a nebulizer that produces a negative pressure effect in accordance with the second preferred embodiment of the present invention.

When the elastic plug is plugged into the carrying cavity 22, both sides of the elastic plug are compressed and the elastic plug is deformed to retract the latch portion 242 and plug the elastic plug into an inner side of the tenon 221. Now, the air originally situated in the carrying cavity 22 is pushed out from the one-way exhaust valve 241 by elastic plug. When the elastic plug is released, the elastic plug is no longer compressed and it returns to its original form. Now, the latch portion 242 is latched to an inner side of the tenon 221 to close the carrying cavity 22 and avoid air leakage. Some air is discharged from the one-way exhaust valve 241 while plugging the elastic plug, and the volume of the carrying cavity 22 substantially remains the same before and after the elastic plug is plugged, so that the pressure in the carrying cavity 22 is smaller than the atmospheric pressure and becomes a negative pressure state which facilitate the nebulized liquid and external air to have an exchange by the nebulizing plate for an effective nebulization.

Figure 6:
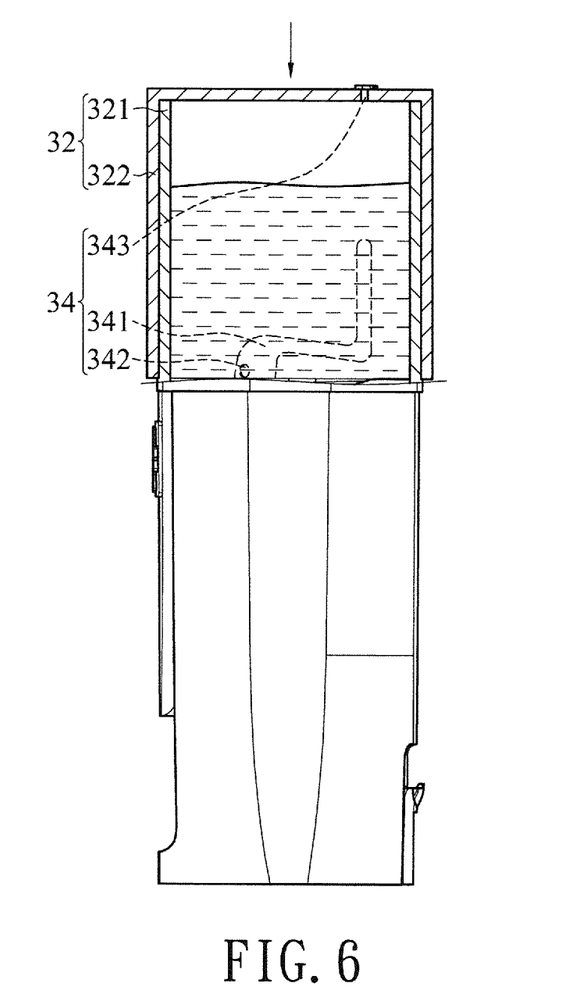
FIG. 6 is a first schematic view of a nebulizer that produces a negative pressure effect in accordance with a third preferred embodiment of the present invention.
Figure 7:
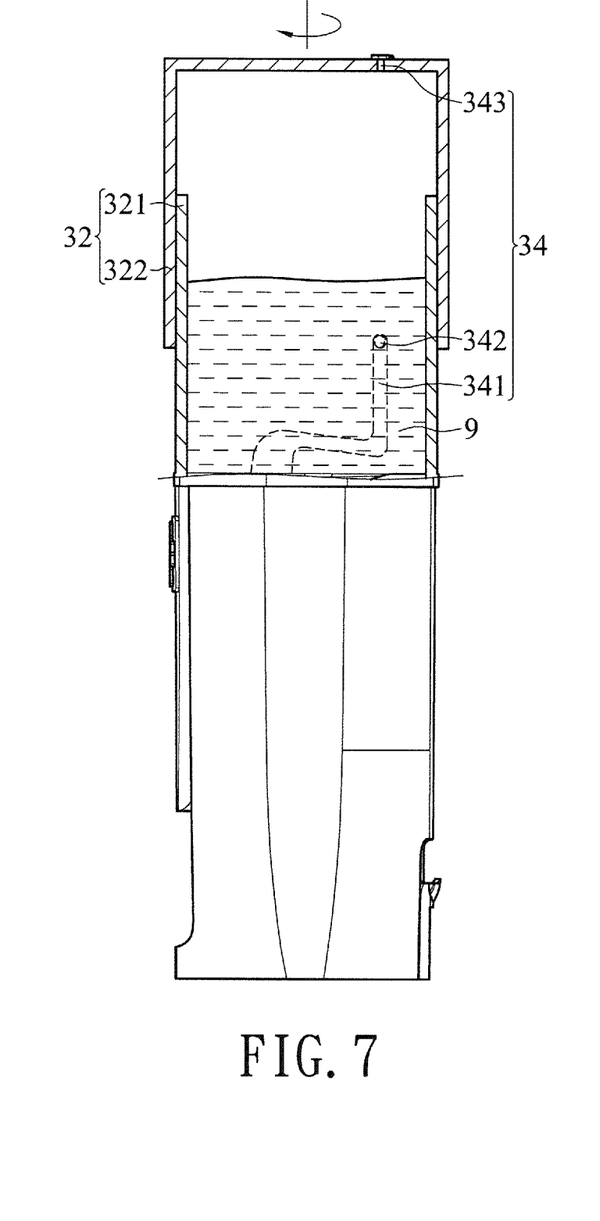
FIG. 7 is a second schematic view of a nebulizer that produces a negative pressure effect in accordance with the third preferred embodiment of the present invention.

With reference to FIGS. 6 and 7 for the third preferred embodiment of the present invention, the difference between this preferred embodiment and the previous preferred embodiments resides on the structure of the carrying cavity 32 and the negative pressure generating element 34 only, and the structure and functions of other elements are the same as those of the previous preferred embodiments and thus will not be repeated.

In FIGS. 6 and 7, the carrying cavity is comprised of an inner cup body 321 and an outer cup body 322, and the negative pressure generating element 34 is comprised of an embedding slot 341, a protrusion 342 and a one-way exhaust valve 343, and the embedding slot 341 is a curve groove formed on the inner cup body 321, and the protrusion 342 is disposed on an inner side of the outer cup body 322 and latched into the embedding slot 341, and the outer cup body 322 is fixed onto the inner cup body 321. However, the present invention is not limited to the arrangement of this preferred embodiment only, but the embedding slot 341 can also be formed on an outer side of the inner cup body 321 or an inner side of the outer cup body 322, and the protrusion 342 can be disposed on an inner side of the outer cup body 322 or an outer side of the inner cup body 321 and opposite to the embedding slot 341, and the protrusion 342 is latched into the corresponding embedding slot 341. The one-way exhaust valve 343 is installed at the top of the outer cup body 322.

When the outer cup body 322 is pulled in a direction away from the inner cup body 321, the protrusion 342 is moved along the groove of the embedding slot 341 and latched to the bottom of the embedding slot 341. Now, the volume of the carrying cavity 32 is increased, and the one-way exhaust valve 343 has the features of allowing air to exit only but not enter, so that the number of air molecules in the carrying cavity 32 remains unchanged, and the carrying cavity 32 produces a negative pressure state to facilitate an exchange of the nebulized liquid and external air for a nebulization.

Figure 8:
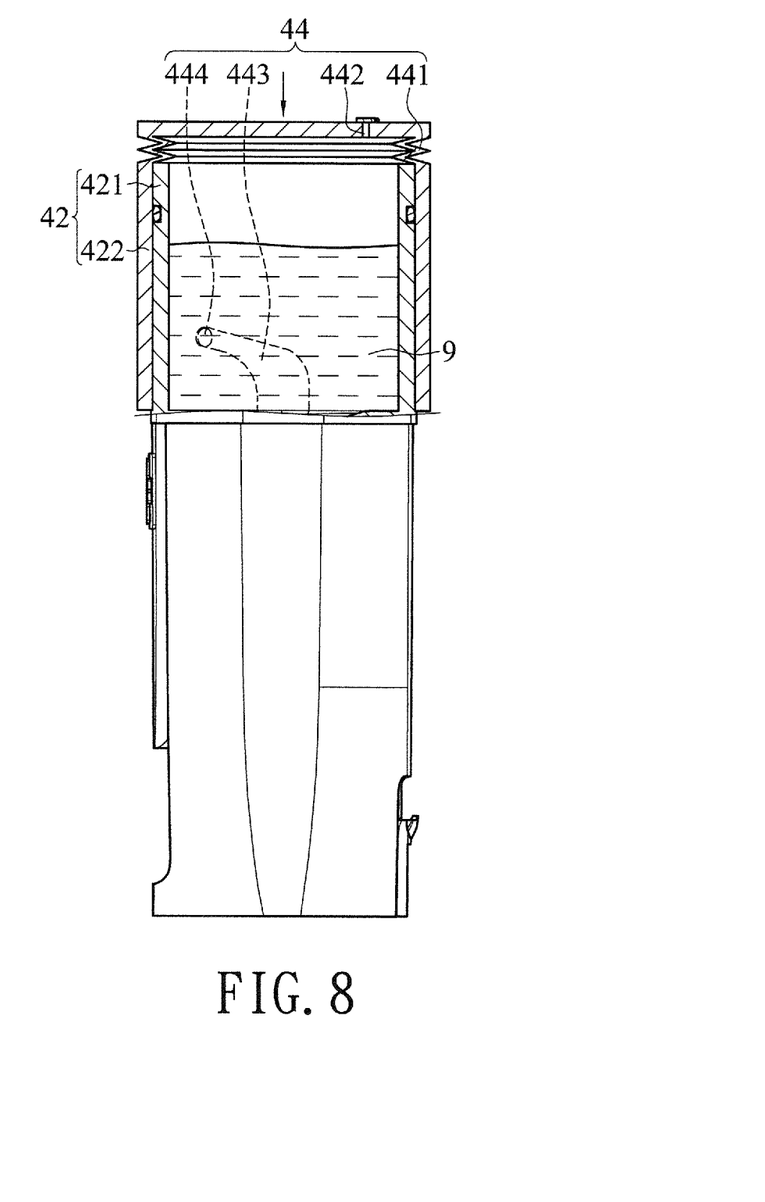
FIG. 8 is a first schematic view of a nebulizer that produces a negative pressure effect in accordance with a fourth preferred embodiment of the present invention.
Figure 9:
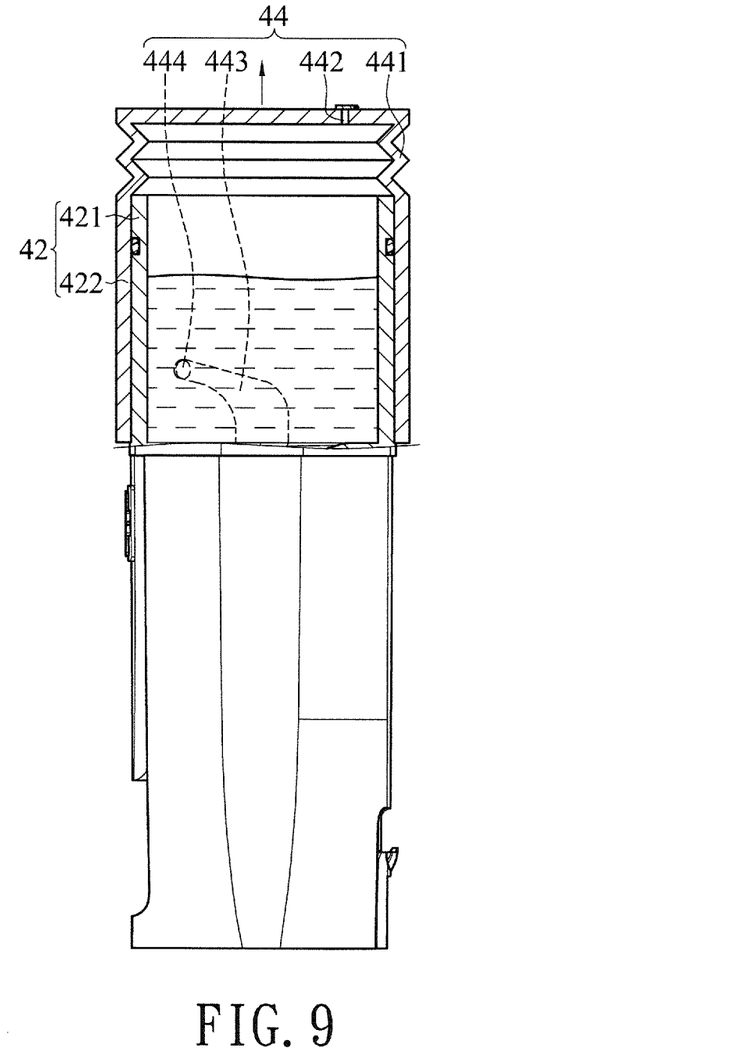
FIG. 9 is a second schematic view of a nebulizer that produces a negative pressure effect in accordance with the fourth preferred embodiment of the present invention.

With reference to FIGS. 8 and 9 for the fourth preferred embodiment of the present invention, the difference between this preferred embodiment and the previous preferred embodiments resides on the structure of the carrying cavity 42 and the negative pressure generating element 44 only, and the structure and functions of other elements are the same as those of the previous preferred embodiments and thus will not be repeated.

In FIGS. 8 and 9, the carrying cavity 42 is comprised of an inner cup body 421 and an outer cup body 422, and the negative pressure generating element 44 is comprised of a telescopic body 441, a one-way exhaust valve 442, a latch groove 443 and a protrusion 444, and the telescopic body 441 and the one-way exhaust valve 442 are disposed at the top of the outer cup body 422, and the protrusion 444 is disposed on an inner side of the inner cup body 421 or an outer side of the outer cup body 422, and the latch groove 443 is formed on an inner side of the outer cup body 422 or an outer side of the inner cup body 421 and opposite to the protrusion 444, and the protrusion 444 is latched into the latch groove 443. Wherein, the telescopic body 441 is made of plastic and has an elastic property when it is pulled and pushed.

When the telescopic body 441 is pulled in a direction away from the inner cup body 421, the telescopic body 441 is propped open and expanded outwardly, so that the volume of carrying cavity 42 becomes bigger. Since the one-way exhaust valve 442 only allows the air to exit but not enter, therefore the number of molecules of the air in the carrying cavity 42 remains unchanged, and the pressure of the air in the carrying cavity 42 is smaller than the atmospheric pressure, so as to produce a negative pressure state and facilitate an exchange of the nebulized liquid and outside air by the nebulizing plate for a nebulization.

Figure 10:
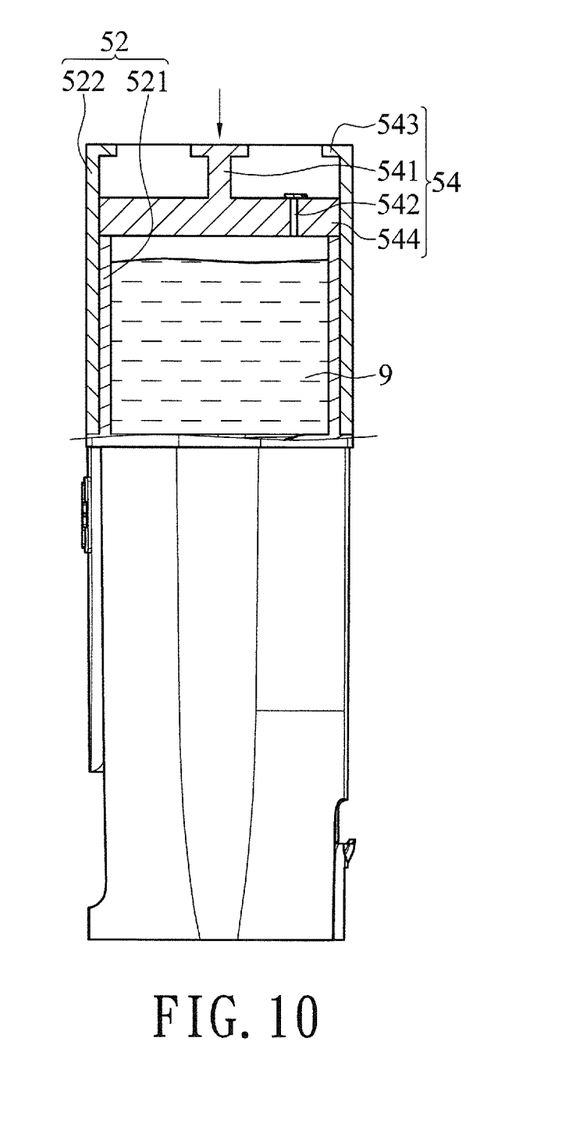
FIG. 10 is a first schematic view of a nebulizer that produces a negative pressure effect in accordance with a fifth preferred embodiment of the present invention.
Figure 11:
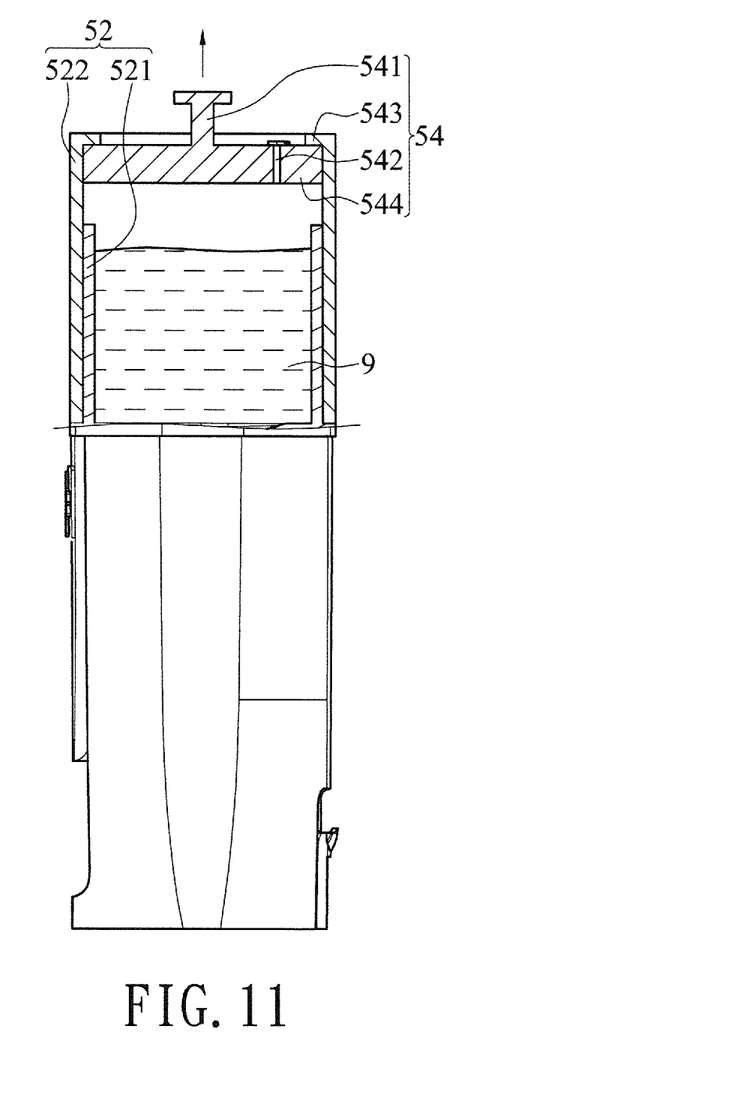
FIG. 11 is a second schematic view of a nebulizer that produces a negative pressure effect in accordance with the fifth preferred embodiment of the present invention.

With reference to FIGS. 10 and 11 for the fifth preferred embodiment of the present invention, the difference between this preferred embodiment and the previous preferred embodiments resides on the structure of the carrying cavity 52 and the negative pressure generating element 54 only, and the structure and functions of other elements are the same as those of the previous preferred embodiments and thus will not be repeated.

In FIGS. 10 and 11, the carrying cavity 52 is disposed in the nebulization body and extended upwardly, and the carrying cavity 52 is comprised of an inner cup body 521 and an outer cup body 522, and the inner cup body 521 is provided for carrying a nebulized liquid 9. The inner cup body 521 has a containing space formed therein for carrying the nebulized liquid 9. The outer cup body 522 is fixed on an outer wall of the inner cup body 521, and the negative pressure generating element 54 is comprised of a piston rod 541, a one-way exhaust valve 542, a tenon 543 and a latch portion 544, and the piston rod 541 is installed at the top of the outer cup body 525 and slidably disposed on an inner wall of the outer cup body 522, and the one-way exhaust valve 542 is installed on a side of the piston rod 541, and the tenon 543 is disposed on a side of the outer cup body 522, and the latch portion 544 is formed on a side of the piston rod 541 and corresponding to the tenon 543 of the outer cup body 522 to latch the piston rod 541 to the outer cup body 522.

When the piston rod 541 is pressed, the volume of the carrying cavity 52 is decreased, and the piston rod 541 is moved downwardly to the top of the inner cup body 521, so that some air is discharged from the one-way exhaust valve 241. When the piston rod 541 is pulled upwardly to the tenon 543, the volume of the carrying cavity 52 is increased. Since the one-way exhaust valve 542 can prevent external air from entering into the carrying cavity 52, therefore the pressure of air in the carrying cavity 52 is smaller than the atmospheric pressure to produce a negative pressure state to facilitate an exchange of the nebulized liquid and external air by the nebulizing plate for a nebulization.

In summation of the description above, the nebulizer with a negative pressure structure installed in the nebulizer in accordance with the present invention can be used for expanding the volume of the carrying cavity or removing air from the carrying cavity to reduce the air pressure of the carrying cavity, so that the carrying cavity is situated in a negative pressure state to improve the effect of nebulizing a liquid of a low surface tension or a high viscosity.

What is claimed is:

1. A nebulizer with a negative pressure structure, comprising:
a nebulization body;
   a carrying cavity, formed in the nebulization body, for carrying a nebulized liquid, and having a through hole and a one-way exhaust valve, which only allows air to exit but not enter the carrying cavity;
   a nebulizing element, installed at the through hole, and comprising:
      a structure plate having an inlet side and an outlet side;
      a piezoelectric driving unit, installed on the outlet side of the structure plate;
      a nebulizing plate, installed on a side of the piezoelectric driving unit, the nebulizing plate being clamped between the piezoelectric driving unit and the structure plate, wherein the carrying cavity is installed on the inlet side of the structure plate; and
a negative pressure generating element, formed right adjacent to the carrying cavity, for changing the volume of the carrying cavity, wherein when the volume of the carrying cavity decreases, the one-way exhaust valve allows air to exit but not enter the carrying cavity, and after the volume of the carrying cavity restored a negative air pressure in the carrying cavity is created, so that a pressure in the carrying cavity is smaller than atmospheric pressure, and an external air will move to a hole of the nebulizing plate, wherein the carrying cavity comprises an inner cup body and an outer cup body, and the negative pressure generating element comprises a pressing portion, the one-way exhaust valve and the pressing portion are disposed at positions of an upper section in the outer cup body, wherein when a user physically and mechanically presses the pressing portion, the pressing portion is moved in a direction towards the inner cup body to decrease a volume occupied by the negative pressure structure and push air in the volume of the negative pressure structure out from the one-way exhaust valve to produces a negative pressure state in the carrying cavity.

* * * * *